US009101676B2

(12) United States Patent
Hoppe et al.

(10) Patent No.: US 9,101,676 B2
(45) Date of Patent: Aug. 11, 2015

(54) METHOD OF OPERATING A VOLATILE MATERIAL DISPENSER

(75) Inventors: Christopher S. Hoppe, Milwaukee, WI (US); Maciej K. Tasz, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 1056 days.

(21) Appl. No.: 12/963,310

(22) Filed: Dec. 8, 2010

(65) Prior Publication Data

US 2011/0132992 A1 Jun. 9, 2011

Related U.S. Application Data

(60) Provisional application No. 61/267,898, filed on Dec. 9, 2009.

(51) Int. Cl.
*A01G 27/00* (2006.01)
*A61L 9/02* (2006.01)
*B05B 17/06* (2006.01)
*B65D 83/26* (2006.01)

(52) U.S. Cl.
CPC .............. *A61L 9/02* (2013.01); *B05B 17/0684* (2013.01); *A61L 2209/11* (2013.01); *B05B 17/0607* (2013.01); *B65D 83/262* (2013.01)

(58) Field of Classification Search
CPC .... A01G 25/16; A01G 25/162; A01G 25/163
USPC .............................. 239/6, 67, 69, 70, 128, 135
See application file for complete search history.

(56) References Cited

U.S. PATENT DOCUMENTS

| | | | |
|---|---|---|---|
| 4,953,763 A * | 9/1990 | Kierum et al. | 222/644 |
| 5,011,632 A | 4/1991 | Yano et al. | |
| 5,297,988 A | 3/1994 | Nishino et al. | |
| 5,591,409 A | 1/1997 | Watkins | |
| 5,884,808 A * | 3/1999 | Muderlak et al. | 222/23 |
| 6,267,297 B1 * | 7/2001 | Contadini et al. | 239/1 |
| 6,554,203 B2 | 4/2003 | Hess et al. | |
| 6,962,496 B2 | 11/2005 | Houri et al. | |
| 7,011,795 B2 | 3/2006 | Thompson et al. | |
| 7,832,655 B2 * | 11/2010 | Tollens et al. | 239/4 |
| 2003/0055879 A1 | 3/2003 | Glass et al. | |
| 2003/0164557 A1 | 9/2003 | Chung et al. | |

(Continued)

FOREIGN PATENT DOCUMENTS

EP 1468702 A1 10/2001
WO 0126448 4/2001

(Continued)

OTHER PUBLICATIONS

PCT/US2010/003126 International Search Report dated Feb. 16, 2011.

*Primary Examiner* — Davis Hwu (57) ABSTRACT

A method of operating a volatile material dispenser includes the step of operating the volatile material dispenser according to a pre-defined algorithm for a first operational cycle. The method further includes the steps of sensing a change in an emission parameter initiated by a user and storing information related to the change in emission parameter. Still further, the method includes the step of operating the volatile material dispenser for a second operational cycle according to a new algorithm, wherein the new algorithm comprises the pre-defined algorithm with modifications according to the change initiated by the user.

18 Claims, 5 Drawing Sheets

(56) References Cited

U.S. PATENT DOCUMENTS

2006/0142968 A1  6/2006  Han et al.
2006/0175426 A1  8/2006  Schramm et al.

FOREIGN PATENT DOCUMENTS

WO  03098971  11/2003
WO  2006064482 A2  6/2006

* cited by examiner

METHOD OF OPERATING A VOLATILE MATERIAL DISPENSER

CROSS REFERENCE TO RELATED APPLICATIONS

This application claims the benefit of U.S. Provisional Application Ser. No. 61/267,898 filed on Dec. 9, 2009, and entitled "Volatile Material Diffuser," the disclosures of which are incorporated herein in their entirety.

REFERENCE REGARDING FEDERALLY SPONSORED RESEARCH OR DEVELOPMENT

Not applicable

SEQUENTIAL LISTING

Not applicable

BACKGROUND

1. Field of the Invention

The present invention relates to devices for dispensing or diffusing a volatile material, and more particularly, to devices for dispensing or diffusing a volatile material having programming for emission of the volatile material.

2. Description of the Background

A multitude of volatile material diffusion devices or diffusers exist in the marketplace. Many of such devices are passive devices that require only ambient air flow to disperse the liquid active material therein. Other devices are battery-powered or receive household power via a plug extending from the device. A cord may be coupled between the plug and the device, or the plug may be mounted directly on the device.

Various means for dispensing volatile materials from volatile material diffusers are also known in the art. For example, some diffusers include a heating element for heating a volatile material to promote vaporization thereof. Other diffusers employ a fan or blower to generate air flow to direct volatile material out of the diffuser into the surrounding environment. In another type of diffuser, one or more volatile materials may be emitted from the diffuser using a bolus generator that delivers a pulse of air to eject a scent ring. Still other diffusers that dispense volatile materials utilize ultrasonic means to dispense the volatile materials therefrom. In addition, other diffusers utilize more than one of these means to vaporize and/or disperse volatile materials.

Many volatile material diffusers include one or more switches or inputs for varying one or more features of the volatile material diffuser. For example, one diffuser includes a heater for evaporating fragrance from a wick that extends from a container to an area adjacent the heater. The diffuser further includes a switch that allows a user to change the power applied to the heater (low, medium, and high). Other diffusers include a knob or other lever that moves the wick toward and away from the heater. A further example of a diffuser includes a piezoelectric element that is disposed adjacent a wick having fragrance therein and extending from a container. The diffuser includes a switch with 5 settings that allow a user to change the frequency of actuation of the piezoelectric element. In particular, the 5 settings correspond to intervals between actuation of the piezoelectric element in milliseconds. It is well known that consumers want to adjust settings on of a diffuser to make a fragrance experience enjoyable for him/her and/or to make a fragrance experience unique to him/her.

SUMMARY OF THE INVENTION

In a first embodiment of the present invention, a method of operating a volatile material dispenser includes the step of operating the volatile material dispenser according to a pre-defined algorithm for a first operational cycle. The method further includes the steps of sensing a change in an emission parameter initiated by a user and storing information related to the change in emission parameter. Still further, the method includes the step of operating the volatile material dispenser for a second operational cycle according to a new algorithm, wherein the new algorithm comprises the pre-defined algorithm with modifications according to the change initiated by the user.

In a second embodiment of the present invention, a method of operating a volatile material dispenser includes the steps of setting an operational cycle for the dispenser and providing power to a diffusion element of the volatile material dispenser according to a first algorithm for a first operational cycle. The method further includes the steps of detecting a change in a user control of the dispenser, storing time information and an emission parameter associated with the change in the user control, and changing the emission parameter. Still further, the method includes the step of providing power to the diffusion element according to a second algorithm for a second operational cycle, wherein the second algorithm is the first algorithm modified according to the detected change.

In a third embodiment of the present invention, a method of operating a volatile material dispenser includes the step of setting an operational cycle for the dispenser and time segments for the operational cycle and providing power to a diffusion element of the volatile material dispenser according to a first algorithm for a first operational cycle. The method further includes the steps of detecting a change in a user control of the dispenser and storing time information, a current time segment, and an emission parameter associated with the user control. Still further, the method includes the step of changing the emission parameter based on the user input for a remainder of the current time segment of the operational cycle or until the user changes the emission parameter for a second time. The method still further includes the steps of saving a second algorithm, which corresponds to the first algorithm modified according to the change in emission parameter and providing power to the diffusion element according to the second algorithm for a second operational cycle.

Other aspects and advantages of the present invention will become apparent upon consideration of the following

DETAILED DESCRIPTION

Figure 1:
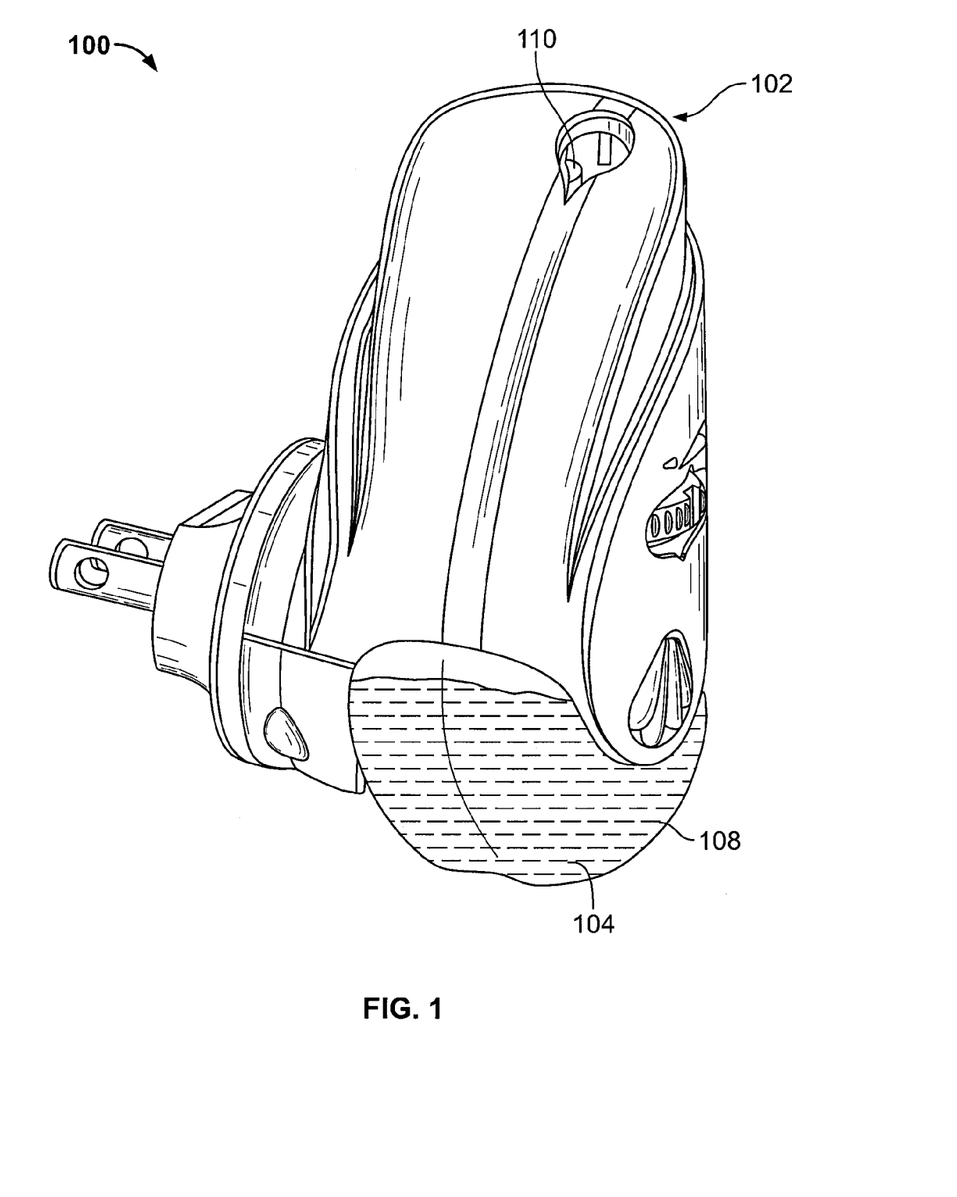
FIG. 1 is a perspective view of a sample device for dispensing a volatile material according to algorithms disclosed herein.
Figure 2:
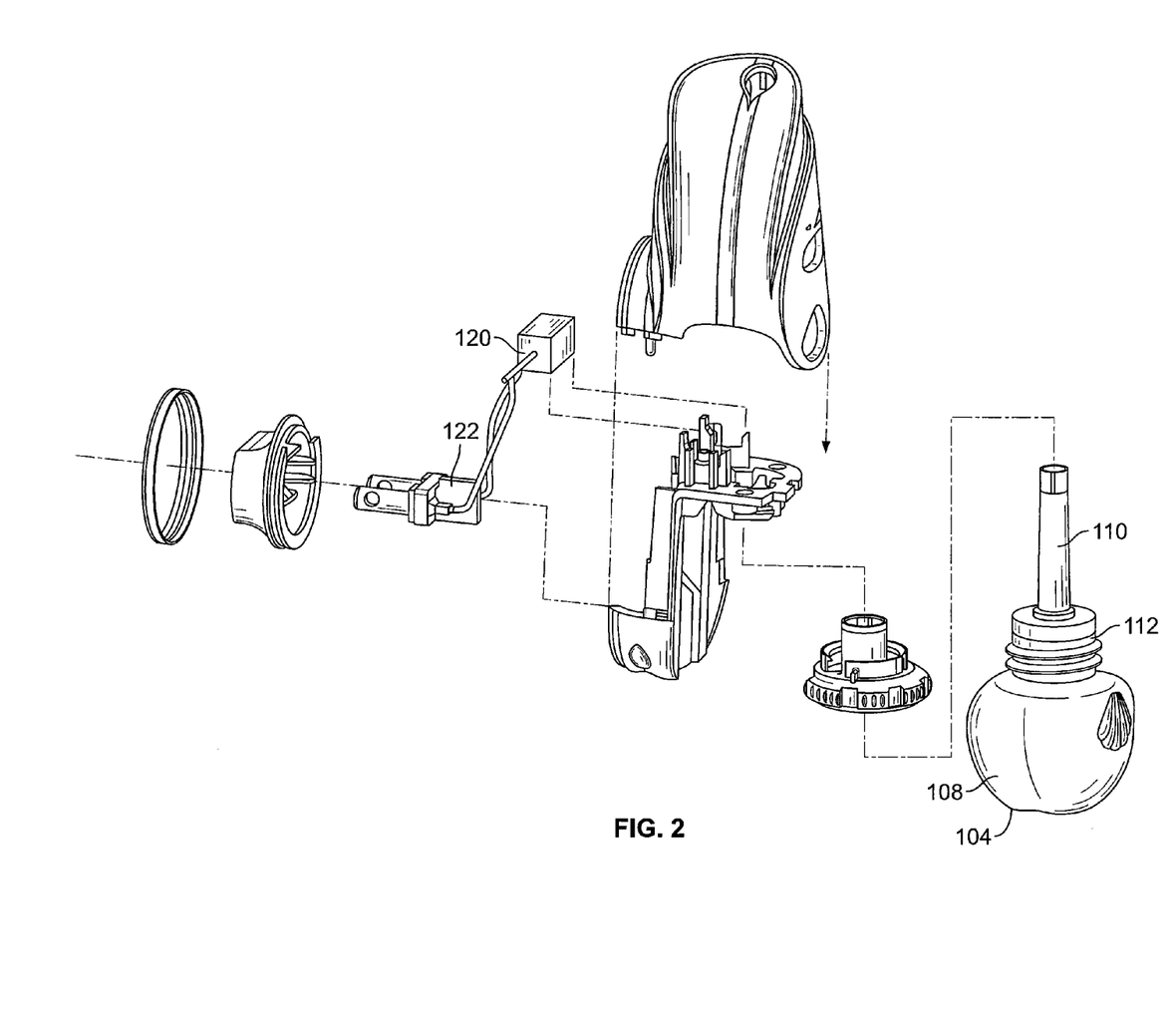
FIG. 2 is an exploded assembly view of the device of FIG. 1.

Referring to FIGS. 1 and 2, a device 100 for dispensing a volatile material comprises a dispenser 102 that is adapted to receive one or more containers, here illustrated as a single container 104. In the illustrated embodiment, the container 104 includes a single compartment that holds a volatile material 108. The volatile material 108 is preferably in the form of a fragrance, but may also be any other volatile substance, such as, for example, an insecticide, an insect repellant, an insect attractant, a disinfectant, a mold or mildew inhibitor, a disinfectant, an air purifier, an aromatherapy scent, an antiseptic, an odor eliminator, a positive fragrancing volatile material, an air-freshener, a deodorizer, or the like, and combinations thereof. The container 104 may alternatively include multiple compartments each holding the same or different volatile materials 108. Still further, two or more containers 108 may be utilized, as seen in the device 150 of FIG. 3. The devices 100, 150 of FIGS. 1 and 2 and FIG. 3, respectively, are described in greater detail in Zobele U.S. Pat. No. 6,996,335 and Porchia et al. U.S. patent application Ser. No. 12/288,606, the disclosures of which are hereby incorporated by reference.

The devices 100, 150 may dispense the one or more volatile materials 108 using one or more selectively actuable diffusion element(s). The diffusion element(s) may comprise one or more heater(s), fan(s), piezoelectric atomizer(s), pump(s), aerosols, and the like, and/or combinations thereof. Alternatively or in addition, the diffusion element may comprise one or more structure(s) that are selectively movable from a closed position to an open position to expose the volatile material(s) 108 to the surroundings, and the volatile material(s) 108 may passively evaporate into the surroundings or may be actively evaporated by one or more additional diffusion elements as noted above. In the illustrated embodiment of FIGS. 1 and 2, the container 104 is a plastic bottle, although the container 104 may alternatively be a metal (or other material) can, a plastic tray with a fragrance gel therein and covered by a vapor permeable membrane, or any other known container utilized for dispensing volatile materials.

Figure 4:
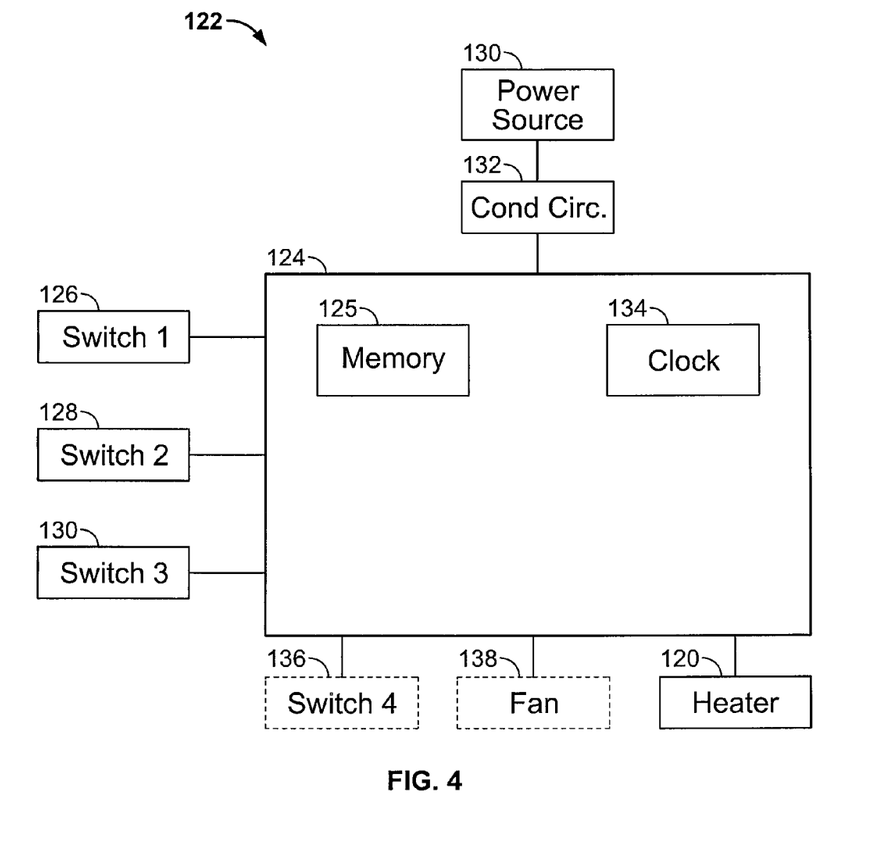
FIG. 4 is a block diagram of circuits including a programmable device for implementing the algorithms disclosed herein within either of the devices of FIGS. 1-3 or any other device for dispensing a volatile material.

Referring again to FIGS. 1 and 2, a single wick 110 is retained in a neck 112 of the container 104 wherein the wick 110 has a first end in fluid communication with the volatile material 108 and a second end that projects outwardly from the container 104. Referring also to FIG. 2, a diffusion element in the form of a heater 120 is disposed adjacent the wick 110 and is selectively energizable by a control apparatus 122 that is mounted in the device 100. Preferably, the control apparatus 122 provides electrical power to the heater 120 according to one or more control algorithms. In the preferred embodiment, the heater 120 is controlled at any particular time by one of a plurality of control algorithms based upon one or more parameters, such as, time of day, current and/or past user settings, type of volatile material 108, etc. Referring to FIG. 4, this functionality is provided by a suitably programmed control circuit, which is preferably an application specific integrated circuit (ASIC) 124. If desired, the control circuit may be a microcontroller or other programmable device or the control circuit may be implemented by firmware or discrete logic components.

Referring to FIG. 4, the ASIC 124 includes internal memory 125 and/or memory external to the ASIC 124. The ASIC 124 is responsive to one or more input devices, such as one or more switches or potentiometers (e.g., rotary, linear, discrete position, continuous position, etc.), buttons (e.g., up/down, or side-by-side buttons), a touch screen, or any other human/machine interface. In one embodiment, the input devices include a first switch 126 that allows a user to turn the device 100 on or off. An optional second switch 128 is provided that has a switch arm, rotary knob, or other structure movable among multiple discrete or continuous positions to allow a user to select the period of an operational cycle, preferably between about 5 minutes and about one month. Optionally, the operational cycle period may be pre-programmed and set to preferably between about 5 minutes and about one month, more preferably between about one day or about one week. Third or more switches 130 of any suitable type permit a user to select one or more emission characteristics, such as: (1) heater duty cycle(s), either as a function of or independent of the selected cycle period and/or the current point in the cycle period and/or time of day, day of week, day of month, or week of month, (2) dwell time(s) for the heater 120, either as a function of or independent of the selected cycle period and/or the current point in the cycle period and/or time of day, day of week, day of month, or week of month, (3) time versus temperature characteristics over a cycle period, etc., and/or other emission characteristics that a consumer would want to alter. If desired, one or both of the second and third switches 128, 130 may be replaced by one or more input devices that permit a user to select from among a plurality of predetermined and stored heater parameter settings that are implemented over predetermined cycle periods. In the illustrated embodiment of FIG. 4, the settings of the second and third switches 128, 130 command operation of the heater 120 by the control apparatus 122 according to one of a plurality of control algorithms dependent upon, among other things, the position of the switch arm.

Optionally, if a diffusion element other than a heater is utilized, the selectable emission characteristics may include, for example, (1) duty cycle(s), either as a function of a selected cycle period and/or a current point in the cycle period and/or time of day, day of week, day of month, or week of month, (2) dwell time(s) for the diffusion element, either as a function of or independent of the selected cycle period and/or the current point in the cycle period and/or time of day, day of week, day of month, or week of month, (3) time versus output over a cycle period, etc., (4) output rate (e.g., speed, frequency, etc., and/or other emission characteristics that a consumer may want to alter.

Electrical power for the electrical components is supplied by residential or commercial 120 volt AC power from a power source 130, in which case suitable power conversion and conditioning circuitry 132 is provided. The device 100 may alternatively utilize batteries for electrical power, in which case suitable circuitry may be provided so that adequate voltage and/or current are supplied to various components to ensure proper operation.

The ASIC 124 also preferably includes an internal clock 134 or other device that knows the time of day, the day of the week, and/or the date. Optionally, the time of day, the day of week, and/or the date may be provided to the ASIC 124 by an external source, such as the atomic clock.

Still referring to FIG. 4, the ASIC 124 repetitively executes programming of a software routine or algorithm on a continuous basis when the device 100 is on. Specifically, referring to FIG. 5, a block 200 of a software routine checks the status of the switch 126 (or any other switch), the status of a sensor (if used; not shown) that detects insertion of a refill container 104 into the device 100, and/or whether AC power is provided by the power source 130. If the switch 126 has been newly moved to the on position, a refill container 104 has been newly inserted, and/or AC power has been newly supplied by the power source 130, then control passes to a block 202, which is an optional part of the programming. The block 202 detects the output of a bar code reader or other identification device (not shown) of the device 100 that reads a bar code or other identification indicia printed on the container 104 that identifies the volatile material 108 in the container 104. If the volatile material 108 in the container 104 is not recognized by the device 100, programming returns to the block 200. If the volatile material 108 is recognized, a block 203 then selects a control algorithm from among a plurality of control algorithms stored in the memory 125 (or stored in external memory) based upon the identification of the volatile material 108 as determined by the block 202. If the block 202 is not included as part of the programming, then a default control algorithm may be selected at the block 203.

Figure 5:
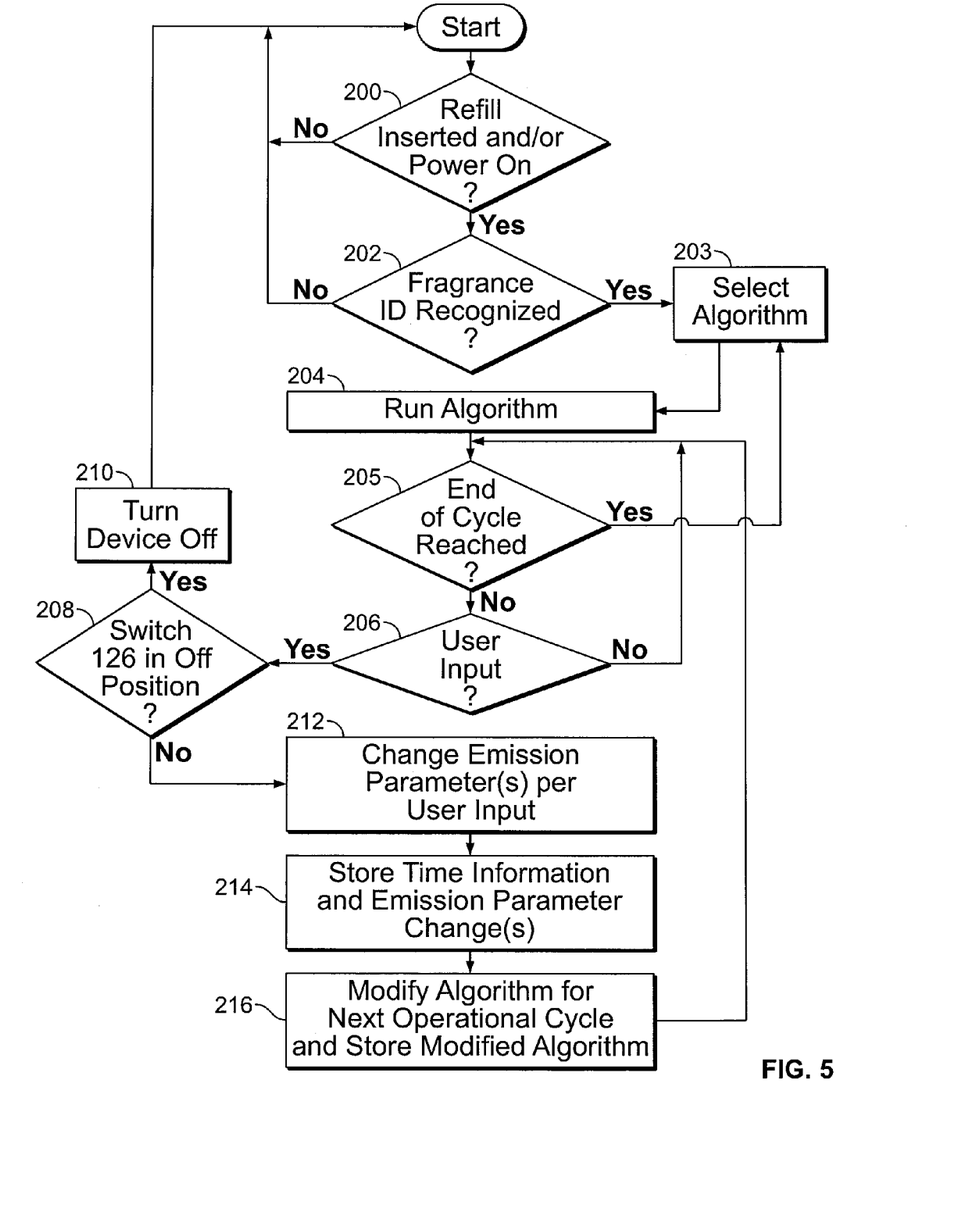
FIG. 5 depicts a flow chart illustrating programming that may be implemented by a programmable device for operation of the devices of FIGS. 1-3 or any other device for dispensing a volatile material.

Following the block 203, a block 204 thereafter operates the heater 120 (or other diffusion element(s)) by providing electrical waveforms thereto based upon the selected control algorithm. A block 205 checks to determine whether an end of the operational cycle has been reached. If so, control passes back to the block 203, which selects a last-saved (or default if no changes have been made) algorithm and control then passes to the block 204 to run the selected algorithm. If the end of the operational cycle has not been reached, following the block 205, a block 206 checks to determine whether a user of the device 100 has provided one or more input commands to the device 100 by moving or actuating the switches 126, 128, and/or 130 (and/or any other switches and/or input devices, if present). If the block 206 determines that no input commands have been provided, then control returns to the block 205. Control remains with the blocks 205 and 206, wherein the heater 120 is operated according to the selected algorithm until one or more input commands have been provided by the user or the end of the operational cycle has been reached. If the end of the operational cycle has been reached, control returns to the block 203, which then selects the last-saved algorithm (or default algorithm if no changes have been made). Once the block 206 determines that one or more input commands has been provided, an optional block 208 checks to determine whether the first switch 126 has been moved to the off position. If this is found to be the case, a block 210 deenergizes the electrical components of the device and, thereafter, control passes back to the block 200.

If the block 208 determines that the switch 126 has not been moved to the off position, a block 212 checks the second and third switches 128 and 130 (and/or any other switches and/or input devices, if present) to determine the input command(s) provided by the user. As noted in greater detail below, the commands may relate to any emission parameter(s) that can be adjusted using the switches 128, 130 (and/or any other input devices). A block 212 implements the input command(s) by changing the emission parameters so that the device 100 immediately switches to a different emission control process in accordance with the input command(s). This is accomplished by modifying the waveforms supplied to the heater 120 (or other diffusion element(s)) in a manner that achieves the commanded effect. Thereafter, a block 214 stores time information developed by the timer 134 and the emission parameter changes in the memory 125 (or in external memory). The time information that is stored is dependent upon the setting of the second switch 128, if utilized or the pre-programmed operational cycle, if utilized. If an operational cycle period is selected via the second switch 128 or pre-programmed to be between 5 minutes and one day in length, then the block 214 stores at least the elapsed time in the current cycle. If the operational cycle period is selected or pre-programmed to be between two days and one week in length, then the block 214 stores at least the current time of day and the current day in the current cycle. If the cycle period is selected or pre-programmed to be greater than one week but does not exceed one month, then the block 214 stores at least the current time of day, the current day of the month, and the current week of the month. Other time information might alternatively or in addition be stored, if desired.

Following the block 214, a block 216 modifies the current control algorithm in accordance with the input command(s) and the stored time information to develop and save a new control algorithm. The effect of this block is discussed in greater detail below. Control then passes back to the block 205, wherein programming determines whether the end of the current operational cycle has been reached. If not, control remains with the blocks 205 and 206 until a user input has been detected or until the end of the current operational cycle has been reached. Every time a user input is detected during the current operational cycle, such input is detected and the selected or current algorithm is modified and saved (with all other non-modified settings remaining the same). If the current operational cycle has ended, control passes from the block 205 to the block 203 wherein the last-saved (or default if no changes have been made) algorithm is selected and control then passes to the block 204, wherein the heater 120 (or other diffusion element(s)) is operated in accordance with the last-saved control algorithm for the next operational cycle. Although the user inputs are saved as the last-saved algorithm, previously saved and/or default algorithms may be saved in the memory 125 for later use, if desired.

The programming of FIG. 5 is continually executed during the entire time that the first switch 126 is in the on position or that AC power is supplied by the power source 130.

As a first example of the operation of the programming of FIG. 5, assume that a user has inserted a container 104 into the device 100 of FIGS. 1 and 2, and that the block 202 has detected a fragrance identification bar code corresponding to the scent Powder Fresh®, a registered trademark of and sold by S.C. Johnson & Sons, Inc. of Racine, Wis. The ASIC 124 selects a control algorithm from the memory 125 (or from external memory) at the block 203 that has been predetermined as the default control algorithm for such scent or for all scents. Specifically, different default algorithms may be set as the default control algorithms for each fragrance or a single default algorithm may be set as the default control algorithm for all fragrances. Optionally, if Powder Fresh® has previously been used in the device 100, the last-saved algorithm for such scent would be selected. Assume also that the operational cycle period is predetermined by the selected control algorithm or is commanded manually by the user to be one day. Assume further that the block 204 causes the selected control algorithm to operate the heater 120 at a high heat setting for a time segment between 7 AM and 9 AM and for a time segment between 6 PM and 10 PM and otherwise operates the heater 120 at a low heat setting for time segments between 12 AM and 7 AM, between 9 AM and 6 PM, and between 10 PM and 12 AM.

Still referring to the first example, if a user on the first day moves the switch 130, for example, to the high heat setting at 12 PM, the block 206 would detect such input and control would pass to the block 208. Assuming the user has not turned off the device 100, control will pass to the block 212 that implements the modified heat setting at 12 PM and the block 214 thereafter stores the time information (12 PM) and the high heat setting. The block 216 thereafter modifies and saves the algorithm for the next operational cycle. Control passes back to the block 205, and control remains with the blocks 205 and 206 (at the high heat setting), since the end of the current operational cycle has not been reached. At 1 PM, the user again moves the switch 130 to the low heat setting. Upon such user input, control passes through the block 208 (assuming the user has not turned the device 100 off) to the block 212 that implements the low heat setting at 1 PM. Thereafter, the block 214 stores the time information (1 PM) and the low heat setting and the block 216 modifies the algorithm for the next operational cycle. If during the first day, the device 100 does not detect any additional user inputs, control passes to the block 203, wherein the last-saved algorithm is selected for the next operational cycle, which is the second day.

In one embodiment, when the user modifies the current algorithm, the modification is only applied to the current time segment. For example, if the user only modified the heat setting at 12 PM in the current example and did not otherwise make any modifications, the time segment encompassing the time 12 PM (9 AM until 6 PM) would be modified accordingly. Again, referring to the current example, the heat setting during the time segment between 9 AM and 6 PM would be set to high. In other words, the heat setting for that time segment would be redefined for the current algorithm. In a different embodiment, once the user modifies the algorithm, the algorithm is then controlled by the user. For example, in the current example, once the user modifies the heat setting at 12 PM to be high, the heater would operate at high until the user again modifies the algorithm. In this example, the heater would operate at high until 1 PM when the user modifies the heat setting to be low. Thereafter, the heater would operate at low until a further user modification or the end of the current operational cycle. In still a further embodiment, the device could be programmed such that sets of modifications to the device settings would modify such settings during a specific time segment and the algorithm would otherwise remain unchanged. Specifically, in the present example, the current algorithm would only be modified during the time segment between 12 PM and 1 PM (to be at a high heat setting), but the current algorithm would otherwise operate as programmed. Still optionally, two or more of such methods of modifying the current algorithm may be utilized.

Figure 3:
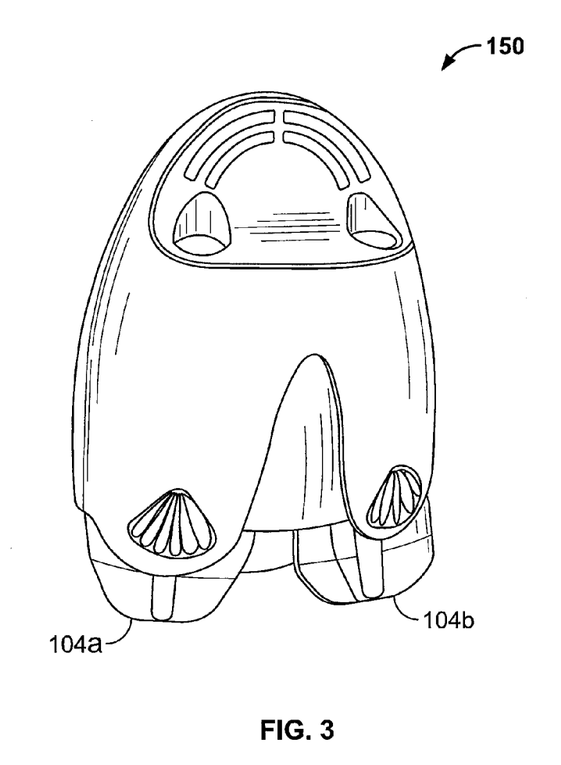
FIG. 3 is a front isometric view of a further sample device for dispensing a volatile material in accordance with the algorithms disclosed herein.

In a second example of operation of the programming of FIG. 5, assume that a switch 130 varies a duty cycle of the heater 120 (10% to 100% in 10% increments), a further switch 136 varies the rotations per minute of a fan 138 (0 RPM to 1600 RPM in 200 RPM increments), a user has inserted two containers 104a, 104b into the device 150 of FIG. 3, and the block 202 has detected fragrance identification bar codes corresponding to the scents Fruit Explosion® and Vanilla Breeze®, registered trademarks of and sold by S.C. Johnson & Sons, Inc. of Racine, Wis. The ASIC 124 selects a control algorithm from the memory 125 (or from external memory) at the block 203 based on one or both of the fragrances or a default algorithm. Optionally, if one of the fragrances or a combination of the fragrances has previously been utilized with the device 150, the last-saved algorithm for such fragrance or combinations of fragrances would be selected. Assume that the operational cycle period is predetermined by the selected control algorithm or is commanded manually by the user to be one week. Assume further that the block 204 causes the selected control algorithm to operate heaters corresponding to the containers 104a, 104b for alternating 45 minute periods, wherein the activated heaters are operated at a 100% duty cycle for time segments between 6 PM and 10 PM Monday through Friday, an 80% duty cycle for time segments between 6 AM and 8 PM Saturday and Sunday, a 40% duty cycle during time segments for all other times of the week. Further a single fan (not shown) disposed within the device 150 operates at 1600 RPM for time segments between 12 PM and 12 AM every day of the week and otherwise operates at 1000 RPM.

In the second example, if a user moves the switch 130 on Monday (the first day), for example, to a 10% duty cycle at 6 AM, the block 206 would detect such input and control would pass to the block 208. Assuming the user has not turned the device 150 off, control passes to the block 212 that implements the modified duty cycle at 6 AM and the block 214 thereafter stores the time information (6 AM) and the duty cycle. The block 216 thereafter modifies the algorithm for the next operational cycle. Since the end of the operational cycle has not been reached, control passes back to the block 205, wherein control remains with the blocks 205 and 206 (at 10% duty cycle). At 6 AM on Wednesday, the user moves the switch 130 back to 80% duty cycle. Upon such user input, control passes through the block 208 (assuming the user has not turned the device 150 off) to the block 212 that implements the 80% duty cycle and thereafter, the block 214 stores the time information (6 AM) and the 80% duty cycle and the block 216 modifies the algorithm for the next operational cycle. If, during the first week, the device 150 does not detect any additional user inputs, control passes to the block 203, wherein the last-saved algorithm is utilized for the next operational cycle. During the next operational cycle, if sets of modifications are utilized to modify the current algorithm, the algorithm would run with all of the default settings except that the duty cycle for the time segment between Monday at 6 AM and Wednesday at 6 AM would be set to 10%.

In a third example of programming of FIG. 5, assume that a user has inserted a container 104 into the device 100 of FIGS. 1 and 2, and that the block 202 has detected a fragrance identification bar code corresponding to the scent Powder Fresh®, a registered trademark of and sold by S.C. Johnson & Sons, Inc. of Racine, Wis. The ASIC 124 selects a control algorithm from the memory 125 (or from external memory) at the block 203, as discussed in detail above with respect to the first example. Assume also that the operational cycle period is predetermined by the selected control algorithm or is commanded manually by the user to be 28 days. Assume further that the block 204 causes the selected control algorithm to operate the heater 120 at a high heat setting for time segments between 7 AM and 9 AM every day and for time segments between 6 PM and 10 PM days 15-28 and otherwise operates the heater 120 for all other time segments at a low heat setting.

Still referring to the third example, if a user on days 1-14 moves the switch 130, for example, to the high heat setting at 6 PM, the block 206 would detect such input and control would pass to the block 208. Assuming the user has not turned off the device 100, control will pass to the block 212 that implements the modified heat setting at 6 PM and the block 214 thereafter stores the time information (6 PM) and the high heat setting. The block 216 thereafter modifies the algorithm for the next operational cycle. Since the end of the operational cycle has not been reached, control passes back to the block 205, wherein control remains with the blocks 205 and 206 (at the high heat setting). At 10 PM each of days 1-14, the user moves the switch 130 back to the low heat setting. Upon such user input, control passes through the block 208 (assuming the user has not turned the device 100 off) to the block 212 that implements the low heat setting at 10 PM. Thereafter, the block 214 stores the time information (10 PM) and the low heat setting and the block 216 modifies the algorithm for the next operational cycle. If during the 28 day operational cycle, the device 100 does not detect any additional user inputs, control passes to the block 204, wherein the last-saved algorithm is utilized. If sets of modifications are utilized to modify the current algorithm, then the last-saved algorithm would have a high heat setting for time segments between 7 AM and 9 AM and for time segments between 6 PM and 10 PM on days 1-28 and would have a low heat setting for all other time segments.

Any of the example algorithms disclosed herein, may be modified by user input during any operational cycle and the algorithms can be modified any number of times. Additionally, the algorithms can account for various settings for one or more diffusion elements within the device 100, 150 and modification of all of such settings.

Although in the specific embodiments disclosed herein, a container having a wick extending therefrom is utilized, depending on the type of diffusion element(s) utilized, a wick may not be necessary. For example, if one or more aerosols are utilized, an aerosol container having a valve stem extending therefrom a nozzle disposed over the valve stem for actuation thereof may be utilized. In another example, of one or more pumps are utilized, a container having a dip tube connected to a pump and a nozzle may be disposed in/on the container for actuation thereof. Still further, different types of diffusion elements may required different types of containers having different means by which volatile material travels to an outside of the container.

Industrial Applicability

The present invention provides programming for a software routine or algorithm. The programming runs an algorithm for an operational cycle and utilizes user inputs to modify the algorithm during the operational cycle. If a modification has been by the user in a previous operational cycle, such modification(s) is implemented in the next operational cycle.

Numerous modifications will be apparent to those skilled in the art in view of the foregoing description. Accordingly, this description is to be construed as illustrative only and is presented for the purpose of enabling those skilled in the art to make and use the present invention and to teach the best mode of carrying out same. All patents and other references cited herein are incorporated by reference in their entirety. The exclusive rights to all modifications which come within the scope of the appended claims are reserved.

We claim:

1. A method of operating a volatile material dispenser, the method comprising the steps of:
    setting an operational cycle for the dispenser, wherein the operational cycle is between about one day and about one week;
    providing power to a heater of the volatile material dispenser according to a first algorithm for a first operational cycle that has a length that is the same as a length of the operational cycle, wherein the heater is actuated for the entire first operational cycle and is disposed within the volatile material dispenser and adjacent a portion of a wick extending from a container holding a volatile material therein to volatilize volatile material contained in the wick;
    detecting a change in a user control of the dispenser during operation of the first algorithm;
    storing time information related to the specific time of day of the change and an emission parameter associated with the change in the user control;
    changing the emission parameter; and
    providing power to the heater according to a second algorithm for a second operational cycle that has a length that is the same as the length of the operational cycle, wherein the heater is actuated for the entire second operational cycle and wherein the second algorithm is the first algorithm modified according to the detected change with the detected change implemented at the specific time of day at which the detected change was made during the first operational cycle.

2. The method of claim 1, wherein the operational cycle is one day and the detected change is implemented by the second algorithm to run the second algorithm on each subsequent day until a further change is detected.

3. The method of claim 1, further including the step of detecting a second change in a user control of the dispenser and storing second time information and a second emission parameter associated with the change in the user control.

4. The method of claim 3, wherein the first-named user control is different than the second-named user control.

5. The method of claim 3, further including the steps of changing the second emission parameter and running a third algorithm that is the first algorithm modified by the first and second changes.

6. The method of claim 1, wherein the emission parameter is selected from a duty cycle, a time versus temperature characteristic, time versus output, and output rate.

7. The method of claim 1, wherein the second operational cycle follows the first operational cycle and the dispenser is turned off between the first and second operational cycles.

8. The method of claim 1, further including the step of reading an identification source on a volatile material refill and selecting the first algorithm from a number of pre-defined algorithms based on a characteristic of the refill.

9. The method of claim 8, wherein the characteristic is the type of volatile material.

10. A method of operating a volatile material dispenser, the method comprising the steps of:
    setting an operational cycle for the dispenser and time segments for the operational cycle, wherein the operational cycle is between about one day and about one week;
    providing power to a heater of the volatile material dispenser according to a first algorithm for a first operational cycle that has a length that is the same as a length of the operational cycle, wherein the heater is disposed within the volatile material dispenser and adjacent a portion of a wick extending from a container holding a volatile material therein to volatilize volatile material contained in the wick;
    detecting a change in a user control of the dispenser during operation of the first algorithm;
    storing time information related to the specific time of day of the change, a current time segment, and an emission parameter associated with the change in the user control;
    changing the emission parameter based on the change for a remainder of the current time segment of the operational cycle or until the user changes the emission parameter for a second time;
    saving a second algorithm, which corresponds to the first algorithm modified according to the change in emission parameter with the change in emission parameter implemented at the specific time of day at which the detected change was made during the first operational cycle; and
    after the first operational cycle is complete, providing power to the heater according to the second algorithm for a second operational cycle that has a length that is the same as the length of the operational cycle.

11. The method of claim 10, wherein the emission parameter is selected from a duty cycle, a time versus temperature characteristic, time versus output, and output rate.

12. A method of operating a volatile material dispenser, the method comprising the steps of:
provose power to a heater of a volatile material dispenser according to a first algorithm for a first operational cycle, wherein the heater is disposed within the volatile material dispenser and adjacent a portion of a wick extending from a container holding a volatile material therein to volatilize volatile material contained in the wick;
detecting a first change in a user control of the volatile material dispenser during operation of the first algorithm;
storing information related to the first change in the user control, including a first emission parameter and first time information related to a first specific time of day of the first change;
detecting a second change in a user control of the volatile material dispenser during operation of the first algorithm;
storing information related to the second change in the user control, including a second emission parameter and second time information related to a second specific time of day of the second change;
saving a second algorithm that is the first algorithm modified by changing the first emission parameter at the first specific time of day and changing the second emission parameter at the second specific time of day;
providing power to the heater according to a second algorithm for a second operational cycle that has a length that is the same as a length of the first operational cycle, wherein the second algorithm is the first algorithm modified according to the detected change.

13. The method of claim 12, wherein the first and second operational cycles are each one day.

14. The method of claim 12, wherein the first and second operational cycles are each one week.

15. The method of claim 12, wherein the first and second operational cycles are each one month.

16. The method of claim 12, further including the step of modifying a last-saved algorithm to create a further new algorithm each time a change in emission parameter is detected.

17. The method of claim 12, further including the step of reading an identification indicium printed on a volatile material refill container that identifies the volatile material and if the volatile material is recognized, selecting a pre-defined algorithm from a number of pre-defined algorithms based on a characteristic of the refill, and if the volatile material is not recognized repeating the step of reading the identification indicium.

18. The method of claim 17, wherein the characteristic is the type of volatile material.

* * * * *